(12) United States Patent
Quirke

(10) Patent No.: US 11,577,041 B2
(45) Date of Patent: Feb. 14, 2023

(54) DEVICE MOUTHPIECE

(71) Applicants: MD DIAGNOSTICS LIMITED, Maidstone (GB); CAMBRIDGE SENSORS LIMITED, Godmanchester (GB)

(72) Inventor: Daniel Quirke, Otham (GB)

(73) Assignees: MD DIAGNOSTICS LIMITED, Maidstone (GB); CAMBRIDGE SENSORS LIMITED, Godmanchester (GB)

(*) Notice: Subject to any disclaimer, the term of this patent is extended or adjusted under 35 U.S.C. 154(b) by 425 days.

(21) Appl. No.: 15/368,522

(22) Filed: Dec. 2, 2016

(65) Prior Publication Data

US 2018/0153441 A1  Jun. 7, 2018

(51) Int. Cl.
*A61M 15/00* (2006.01)
*A61M 16/10* (2006.01)

(52) U.S. Cl.
CPC .... *A61M 16/1065* (2014.02); *A61M 16/1055* (2013.01); *A61M 15/0021* (2014.02)

(58) Field of Classification Search
CPC .............. A61M 16/105; A61M 16/106; A61M 16/107; A61M 16/1065; A61M 16/1055; A61M 16/0488; A61M 16/049; A61M 15/0021
USPC ........................................................ 600/543
See application file for complete search history.

(56) References Cited

U.S. PATENT DOCUMENTS

| | | | | |
|---|---|---|---|---|
| 3,782,083 A | * | 1/1974 | Rosenberg | B01D 46/10 55/491 |
| 3,797,479 A | * | 3/1974 | Graham | A61B 5/083 600/538 |
| 5,390,668 A | * | 2/1995 | Lehman | A61B 5/097 128/205.27 |
| 6,244,865 B1 | * | 6/2001 | Nelson | A61B 5/097 128/205.29 |
| 2009/0044597 A1 | * | 2/2009 | Kvasnik | A61B 5/097 73/23.3 |
| 2015/0065903 A1 | * | 3/2015 | Colman | F16L 37/244 600/532 |
| 2015/0119744 A1 | * | 4/2015 | Lawson | A61B 5/09 600/539 |

FOREIGN PATENT DOCUMENTS

EP  2098166 A1 * 9/2009 ............. A61B 5/097

* cited by examiner

*Primary Examiner* — Daniel L Cerioni
*Assistant Examiner* — Deirdre M Willgohs
(74) *Attorney, Agent, or Firm* — Liang & Hennessey LLP; Brian Hennessey

(57) ABSTRACT

A device mouthpiece is provided wherein the mouthpiece comprises a cylindrical tube and a filter element, wherein the filter element comprises a frame and a filter medium secured to the frame; the frame defines an annular channel which receives therein an end portion of the cylindrical tube; the end portion of the cylindrical tube forms a friction fit within the annular channel; and wherein the filter element is secured to the cylindrical tube via the friction fit.

15 Claims, 1 Drawing Sheet

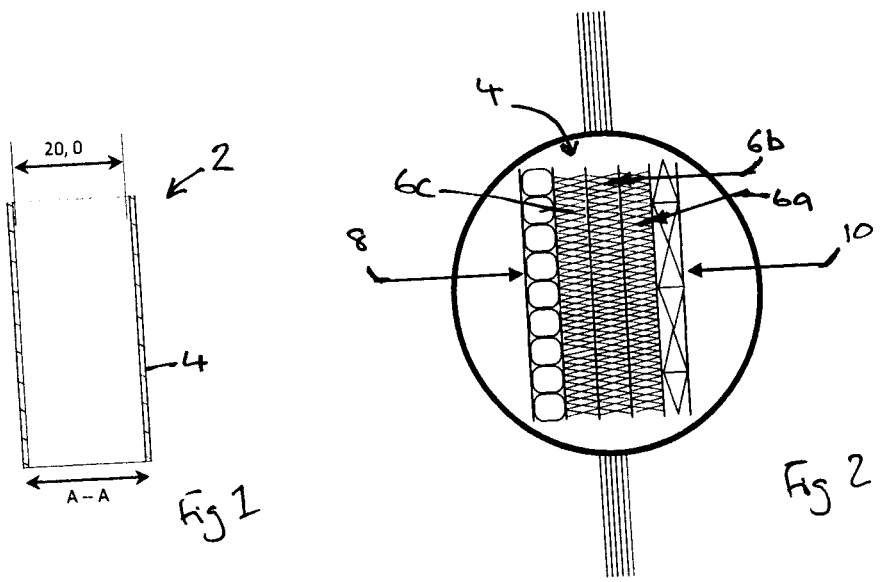
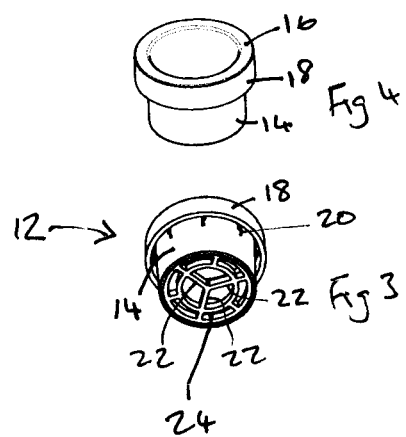

DEVICE MOUTHPIECE

The present invention relates to mouthpieces for devices, such as diagnostic or therapeutic respiratory devices. In particular it relates to filtered mouthpieces.

Many devices have been designed to analyse certain features relating to a subject from a breath sample. Such devices include carbon monoxide (CO) detectors which are used to detect levels of carbon monoxide in the exhaled gases of a subject, hydrogen breath detectors which are similar to CO detectors, but which measure levels of hydrogen in the exhaled gases, and alcohol detectors which measure a breath alcohol level and are often used to measure intoxication.

The devices are typically relatively expensive and are designed to be re-used multiple times. However the breath of a subject is a warm, moist environment and therefore often contains numerous microbes, such as bacteria and viruses. It is therefore desirable to allow a sample of exhaled gases to enter the device, but to prevent microbes associated with the exhaled gases to reach the device to prevent a microbiological build-up in the device. Such a build-up of microbiological matter may pose an infection risk for subsequent users of the device. It is also desirable to prevent particulate matter that may also be associated with exhaled gases to enter the device and thereby impair the sensor components of the device.

According to a first aspect of the invention, there is provided a device mouthpiece comprising a cylindrical tube and a filter element, wherein the filter element comprises a frame and a filter medium secured to the frame; the frame defines an annular channel which receives therein an end portion of the cylindrical tube; the end portion of the cylindrical tube forms a friction fit within the annular channel; and wherein the filter element is secured to the cylindrical tube via the friction fit. The device mouthpiece of the invention is suitably disposable and may be intended for single patient use. The patient may use the mouthpiece on multiple occasions or they may use it for a single use. The cylindrical tube forms a conduit to direct exhaled gases into a gas analyser and the filter medium allows gases to pass therethrough, but prevents the passage therethrough of micro-biological matter (microbes), saliva and/or particulate material. As the filter medium is intended to capture the microbiological matter, saliva and/or particulate material and is disposable, the risk of infection to subsequent users, each of whom would use a new, unused device mouthpiece is minimised.

The filter element includes a portion which fits over one end of the cylindrical tube. This is in the form of an annular channel defined by the frame which is sized and configured to receive therein an end portion of the cylindrical tube. The filter element may additionally or alternatively include a substantially cylindrical body portion which in use is located within the cylindrical tube. The substantially cylindrical body portion may form a tight or friction fit within the cylindrical tube. The annular channel may be located at one end of the cylindrical body portion.

The cylindrical tube forms a friction fit within the annular channel. This has the effect of coupling the filter element to the cylindrical tube. In order to form the friction fit more securely, at least one surface of the annular channel may include a plurality of radially extending ribs. Thus, the annular channel may define an inner wall (e.g. a portion of the cylindrical body portion) which has an outwardly facing surface, and an outer wall or skirt which is spaced from the inner wall and has an inwardly facing surface, wherein the cylindrical tube in use is located between the outwardly facing surface of the inner wall and the inwardly facing surface of the outer wall. The outwardly facing surface of the inner wall may carry or define radially outwardly extending ribs and/or the inwardly facing surface of the outer wall may carry or define radially inwardly extending ribs. The ribs are configured to bite into the wall of the cylindrical tube when an end of it is urged into the annular channel and thereby increase the friction between the filter element and the cylindrical tube.

The ribs may be circumferentially spaced around the annular channel.

In order to trap micro-biological matter without restricting unduly airflow through the medium, the filter medium is suitably an electrostatic filter medium. Optionally, the filter medium is a non-woven electrostatic filter medium, such as a non-woven polymeric electrostatic filter medium.

In an embodiment of the invention, the filter medium is secured to the frame. This may be achieved by locating the filter medium between two spaced apart frame portions (i.e. trapping the filter medium between two portions of the frame) or by fixing or attaching the filter medium to at least a portion of the frame.

The filter element frame may be a polymeric frame, in which case, the filter medium may be attached to at least a portion of the frame via an adhesive and/or via a welding process. Suitably, the filter medium is formed from a polymeric material, the frame is formed from a polymeric material and the filter medium is welded to at least a portion of the filter frame, for example, the filter medium may be ultrasonically welded to the polymeric frame. The weld may extend around the entire circumference of the frame. By forming a weld between the filter medium and the frame around the entire circumference of the frame, no gaps exist between the filter medium and the frame and as such, the filter medium is able to trap a greater percentage of microbes, saliva and/or particulate matter.

The frame may be formed by injection moulding and may therefore be a polymeric, injection moulded frame. The frame may be formed, for example, from a polyalkylene, such as polypropylene.

In an embodiment of the invention, the frame is a polymeric frame which defines an internal cylindrical channel and the filter medium is ultrasonically welded to a portion of the internal cylindrical channel such that the weld extends around the entire circumference of the cylindrical channel. In the context of the present invention, the portion of the internal cylindrical channel to which the filter medium is welded includes the annular end face of the cylindrical channel.

By securing the filter medium to the frame, the filter medium is able to filter a majority of the exhaled gases passing through the filter element. Adhering the filter medium to the frame provides a better seal between the filter medium and the frame which reduces the volume of unfiltered gases able to pass through the filter element. However, ultrasonically welding the filter medium around the entire circumference of the frame provides a still better seal between the filter medium and the frame which reduces still further the volume of unfiltered gases able to pass through the filter element.

In order to support the filter medium in use, the frame may define an internal cylindrical channel and two or more radial support elements which extend across the channel. The radial support elements may reduce axial deflection of the filter medium in use. By supporting the filter medium in this way, the risk of accidental swallowing of the filter medium is reduced.

As noted above, the device mouthpiece is suitably a disposable component. Accordingly, the cylindrical tube is suitably made from a material that is cheap and easy to produce and which is relatively non-damaging to the environment after disposal. Accordingly, the cylindrical tube may be formed from a fibrous material, such as a compressed fibre material, suitably cardboard. The cylindrical tube may comprise a plurality of layers of the fibrous material in order to provide the desired strength characteristics.

The outer surface of the cylindrical tube may be coated with a polymeric barrier layer. The barrier layer prevents direct contact between the user's lips and the fibrous material of the tube. This eliminates the risk of a chemical reaction between the user and chemicals that may be present in the fibrous material; it enhances the seal between the device mouthpiece and the device with which the mouthpiece is being used; and it prevents or reduces the risk of the user's lips sticking to the fibrous material. The barrier layer may be formed from a polyalkylene, such as polyethylene.

The skilled person will appreciate that the features described and defined in connection with the aspect of the invention and the embodiments thereof may be combined in any combination, regardless of whether the specific combination is expressly mentioned herein. Thus, all such combinations are considered to be made available to the skilled person.

An embodiment of the invention will now be described, by way of example only, with reference to the accompanying drawings in which:

FIG. 1 is a cross-section through a cylindrical tube which forms part of the invention;

FIG. 2 is a magnified section through a wall of the cylindrical tube shown in FIG. 1;

FIG. 3 is a perspective view of a filter element which forms part of the invention; and FIG. 4 is a perspective view of the filter element shown in FIG. 3 from a different angle.

For the avoidance of doubt, the skilled person will appreciate that in this specification, the terms "up", "down", "front", "rear", "upper", "lower", "width", etc. refer to the orientation of the components as found in the example when installed for normal use as shown in the Figures.

As shown in FIG. 1, a cylindrical tube 2 is provided which is of a simple, disposable construction. The tube 2 is defined by a wall 4 and is open at both ends. The wall 4 is shown in more detail in FIG. 2, where it can be seen that the wall 4 is a laminate including a core formed from three layers of a Kraft liner paper 6a, 6b, 6c; an outer layer 8 formed from a paper coated with polyethylene; and an inner layer 10 formed from a paper coated with polyvinyl acetate. The layers are adhered together with a polyvinyl acetate adhesive to form the rigid, polymer-coated tube 2. The tube is between 60 and 70 mm long and has an internal diameter of 20 mm and an outer diameter of 22 mm.

FIG. 3 shows a filter element 12 including a cylindrical main body portion 14 which is open at both ends. At one end of the main body portion 14 is an outwardly extending top wall 16 (seen in FIG. 4) and a radially downwardly extending skirt portion 18, wherein the skirt portion 18 is coaxial with the main body portion 14 and spaced outwardly therefrom to define an annular channel between the main body portion 14 and the skirt 18, the channel being closed at one end by the top wall 16 and open at the opposite end.

The top end of the main body portion 14 (i.e. the end adjacent to the top wall 16) includes a plurality of radially outwardly projecting ribs 20. The ribs 20 are circumferentially spaced around the outer surface of the main body portion 14 and extend axially such that they extend beyond the length of the channel.

At the bottom end of the main body portion 14, there is provided three radially inwardly extending supporting arms 22 which meet at the longitudinal axis of the body portion 14. Also provided at the bottom end of the main body portion 14 is an annular supporting ring 24.

An electrostatic filter medium (not shown) is ultrasonically welded to the bottom end of the main body portion 14, such that the weld extends around the entire circumference of the bottom of the main body portion 14. In other words, the electrostatic filter medium is welded to the downwardly facing peripheral wall of the main body portion 14. The filter medium is supported in place by the radial supporting arms 22 and the supporting ring 24, such that it is not able to enter the cylindrical channel defined by the main body portion 14.

The annular channel defined between the main body portion 14 and the skirt 18 is sized to receive therein the cylindrical tube 2. Thus, the outer diameter of the main body portion 14 is 20 mm so that the main body portion 14 fits snugly within the tube 2 and the inner diameter of the skirt 18 is 22.2 mm such that an end portion of the tube 2 is able to fit snugly within the channel. The axial ribs 20 engage the internal surface of the tube 2 such that the main body portion 14 forms a tight friction fit within the tube 2 and the end portion of the tube 2 forms a friction fit within the annular channel. This arrangement resists the removal of the filter element 12 from the tube 2.

The ultrasonic weld between the peripheral edge of the filter medium and the entire circumference of the main body portion 14 prevents any exhaled gases from passing between the filter medium and the main body portion 14. Thus, all exhaled gases must pass through the filter medium whereupon microbes and particulate matter entrained within the flow of exhaled gases are trapped by the filter medium.

In use, the main body portion 14 of the filter element 12 is urged into the top end of the tube 2 until the top end of the tube 2 is located snugly within the annular channel. The bottom end of the tube is then located into a receiving portion of a gas analysing device and a user breathes into the device via the combined tube 2 and filter element 12 (together a "device mouthpiece"). The filter medium filters the exhaled gases and prevents contaminants reaching the device. After use, the device mouthpiece is discarded and a fresh mouthpiece is used for the next user.

What is claimed is:

1. A device mouthpiece comprising:
    a cylindrical tube; and
    a filter element comprising a frame and a filter medium, the frame including a cylindrical main body portion defining an internal cylindrical channel;
    wherein at one end of the cylindrical main body portion is a radially outwardly extending wall portion;
    wherein depending from an outer periphery extending from the wall portion is a skirt;
    wherein the skirt is coaxial with the main body portion and spaced outwardly therefrom to define an annular channel between an outwardly facing surface of the main body portion and an inwardly facing surface of the skirt;
    wherein the annular channel is closed at one end by the outwardly extending wall and open at the other end;

wherein the filter medium is secured to an inwardly facing surface of the cylindrical main body portion;

wherein the annular channel is adapted to receive therein an end portion of the cylindrical tube;

wherein the end portion of the cylindrical tube includes an outwardly facing surface and an inwardly facing surface;

wherein the outwardly facing surface of the cylindrical tube forms a first friction fit with the inwardly facing surface of the skirt of the annular channel, and the inwardly facing surface of the cylindrical tube forms a second friction fit with the outwardly facing surface of the main body portion of the annular channel;

wherein the filter element is secured to the cylindrical tube via the first and second friction fits;

wherein the frame is formed from a polymeric material and the filter medium is ultrasonically welded to a portion of the inwardly facing surface of the cylindrical main body portion such that the weld extends around an entire circumference of the cylindrical channel; and wherein the cylindrical main body portion of the frame and the filter medium are disposed within the cylindrical tube.

2. A device mouthpiece according to claim 1, wherein the inwardly facing surface of the skirt of the annular channel includes a plurality of radially extending ribs.

3. A device mouthpiece according to claim 1, wherein the filter medium is an electrostatic filter medium.

4. A device mouthpiece according to claim 1, wherein two or more radial support elements extend across the internal cylindrical channel.

5. A device mouthpiece according to claim 1, wherein the cylindrical tube comprises a body formed from a fibrous material.

6. A device mouthpiece according to claim 5, wherein the fibrous material is cardboard.

7. A device mouthpiece according to claim 5, wherein the outer surface of the cylindrical tube is coated with a polymeric barrier layer.

8. A device mouthpiece according to claim 1, wherein the filter medium has a first diameter less than a second diameter of the cylindrical tube.

9. A device mouthpiece according to claim 2, wherein the plurality of radially extending ribs extend parallel to an axis defined by the skirt portion and the main body portion.

10. A device mouthpiece according to claim 2, wherein the plurality of radially extending ribs are spaced from each other around a circumference of an axis defined by the skirt and the main body portion.

11. A device mouthpiece according to claim 2, wherein the plurality of radially extending ribs are configured to bite into an end face of the end portion of the cylindrical tube when the annular channel receives the cylindrical tube to further secure the filter element to the cylindrical tube.

12. A device mouthpiece comprising:
a cylindrical tube; and
a filter element comprising a frame and a filter medium, the frame being formed from a polymeric material and including a cylindrical main body portion defining an internal cylindrical channel, a radially outwardly extending wall portion at one end of the cylindrical main body portion, a skirt depending from an outer periphery extending from the wall portion, the skirt being coaxial with the main body portion and spaced outwardly therefrom to define an annular channel between an outwardly facing surface of the main body portion and an inwardly facing surface of the skirt, the annular channel being closed at one end by the outwardly extending wall and open at the other end and adapted to receive therein an end portion of the cylindrical tube;

wherein the filter medium is ultrasonically welded to a portion of the inwardly facing surface of the cylindrical main body portion such that the weld extends around an entire circumference of the cylindrical channel;

wherein an end portion of the cylindrical tube includes an outwardly facing surface and an inwardly facing surface, the outwardly facing surface of the cylindrical tube forming a first friction fit with the inwardly facing surface of the skirt of the annular channel, the inwardly facing surface of the cylindrical tube forming a second friction fit with the outwardly facing surface of the main body portion of the annular channel, the filter element being secured to the cylindrical tube via the first and second friction fits; and wherein the cylindrical main body portion of the frame and the filter medium are disposed within the cylindrical tube.

13. A device mouthpiece comprising:
a cylindrical tube; and
a filter element comprising a frame and adapted to couple to a filter medium, the frame being formed from a polymeric material and including a cylindrical main body portion defining an internal cylindrical channel, a radially outwardly extending wall portion at one end of the cylindrical main body portion, a skirt depending from an outer periphery extending from the wall portion, the skirt being coaxial with the main body portion and spaced outwardly therefrom to define an annular channel between an outwardly facing surface of the main body portion and an inwardly facing surface of the skirt, the annular channel being closed at one end by the outwardly extending wall and open at the other end and adapted to receive therein an end portion of the cylindrical tube;

wherein a portion of the inwardly facing surface of the cylindrical main body portion is adapted to receive the filter medium via ultrasonically welding such that the weld extends around an entire circumference of the cylindrical channel;

wherein an end portion of the cylindrical tube includes an outwardly facing surface and an inwardly facing surface, the outwardly facing surface of the cylindrical tube forming a first friction fit with the inwardly facing surface of the skirt of the annular channel, the inwardly facing surface of the cylindrical tube forming a second friction fit with the outwardly facing surface of the main body portion of the annular channel, the filter element being secured to the cylindrical tube via the first and second friction fits; and wherein the cylindrical main body portion of the frame and the filter medium are disposed within the cylindrical tube.

14. A device mouthpiece according to claim 1, wherein the second friction fit is a thread-less friction fit.

15. A device mouthpiece according to claim 1, wherein the outwardly facing surface of the main body portion of the annular channel includes a plurality of radially extending ribs.

* * * * *